United States Patent
Pan et al.

(10) Patent No.: US 10,789,738 B2
(45) Date of Patent: Sep. 29, 2020

(54) METHOD AND APPARATUS TO REDUCE ARTIFACTS IN A COMPUTED-TOMOGRAPHY (CT) IMAGE BY ITERATIVE RECONSTRUCTION (IR) USING A COST FUNCTION WITH A DE-EMPHASIS OPERATOR

(71) Applicants: THE UNIVERSITY OF CHICAGO, Chicago, IL (US); CANON MEDICAL SYSTEMS CORPORATION, Otawara-shi (JP)

(72) Inventors: Xiaochuan Pan, Chicago, IL (US); Zheng Zhang, Chicago, IL (US); Dan Xia, Chicago, IL (US); Yu-Bing Chang, Albany, NY (US); Jingwu Yao, Buffalo Grove, IL (US); Joseph Manak, Albany, NY (US)

(73) Assignees: THE UNIVERSITY OF CHICAGO, Chicago, IL (US); CANON MEDICAL SYSTEMS CORPORATION, Otawara-shi (JP)

( * ) Notice: Subject to any disclaimer, the term of this patent is extended or adjusted under 35 U.S.C. 154(b) by 147 days.

(21) Appl. No.: 16/179,751

(22) Filed: Nov. 2, 2018

(65) Prior Publication Data
US 2019/0139272 A1  May 9, 2019

Related U.S. Application Data

(60) Provisional application No. 62/581,465, filed on Nov. 3, 2017.

(51) Int. Cl.
*G06T 11/00* (2006.01)
*A61B 6/00* (2006.01)
*A61B 6/03* (2006.01)

(52) U.S. Cl.
CPC ............ *G06T 11/005* (2013.01); *A61B 6/032* (2013.01); *A61B 6/5258* (2013.01); *G06T 11/006* (2013.01); *G06T 2207/10081* (2013.01)

(58) Field of Classification Search
CPC ..... A61B 6/032; A61B 6/5258; G06T 11/005; G06T 11/006; G06T 2207/10081; G06T 2211/424
See application file for complete search history.

(56) References Cited

U.S. PATENT DOCUMENTS 10,573,030 B2 * 2/2020 Keeler ................. G06T 11/008
2001/0028696 A1 * 10/2001 Yamada ................ G06T 11/005
378/4

(Continued)

*Primary Examiner* — Gandhi Thirugnanam
(74) *Attorney, Agent, or Firm* — Oblon, McClelland, Maier & Neustadt, L.L.P.

(57) ABSTRACT

An apparatus and method are provided for computed tomography (CT) imaging to reduce artifacts due to objects outside the field of view (FOV) of a reconstructed image. The artifacts are suppressed by using an iterative reconstruction method to minimize a cost function that includes a de-emphasis operator. The de-emphasis operator operates in the data domain, and minimizes the contributions of data inconsistencies arising from attenuation due to objects outside the FOV. This can be achieved by penalizing images that manifest indicia of artifacts due to outside objects especially those outside objects have high-attenuation densities and minimizing components of the data inconsistency likely attributable to the outside object.

20 Claims, 9 Drawing Sheets

(56) References Cited

U.S. PATENT DOCUMENTS

| | | | | |
|---|---|---|---|---|
| 2002/0177773 A1* | 11/2002 | Natterer | ............... | A61B 6/4258 600/436 |
| 2003/0123718 A1* | 7/2003 | Edic | ..................... | G06T 11/005 382/131 |
| 2007/0116343 A1* | 5/2007 | Sauer | ........................ | G06T 7/11 382/131 |
| 2007/0153970 A1* | 7/2007 | Harding | ............... | G01N 23/046 378/4 |
| 2011/0081071 A1* | 4/2011 | Benson | ................ | G06T 11/005 382/154 |
| 2013/0028500 A1* | 1/2013 | Takahashi | .............. | A61B 6/032 382/132 |
| 2013/0177132 A1* | 7/2013 | Takahashi | ............ | G06T 11/006 378/4 |
| 2013/0215249 A1* | 8/2013 | Papalazarou | ............ | A61B 6/02 348/77 |
| 2013/0243297 A1* | 9/2013 | Koehler | ................ | G06T 11/005 382/131 |
| 2014/0003688 A1* | 1/2014 | Hansis | ................. | A61B 6/4417 382/130 |
| 2014/0193055 A1* | 7/2014 | Takahashi | ............. | G06T 11/006 382/131 |
| 2014/0198892 A1* | 7/2014 | Yamakawa | .............. | A61B 6/03 378/4 |
| 2014/0226887 A1* | 8/2014 | Takahashi | ............... | G06T 5/002 382/131 |
| 2014/0270440 A1* | 9/2014 | Inglese | ................ | A61B 6/5205 382/131 |
| 2014/0328450 A1* | 11/2014 | Pal | ....................... | G01N 23/046 378/5 |
| 2016/0371862 A1* | 12/2016 | Silver | .................... | A61B 6/032 |
| 2017/0196529 A1* | 7/2017 | Lin | ........................ | A61B 6/541 |
| 2017/0340304 A1* | 11/2017 | Qiulin | ................. | A61B 6/5264 |
| 2019/0076101 A1* | 3/2019 | Pan | ........................ | A61B 6/032 |
| 2019/0108441 A1* | 4/2019 | Thibault | ............... | G06T 11/008 |
| 2019/0139272 A1* | 5/2019 | Pan | ....................... | G06T 11/005 |

* cited by examiner

METHOD AND APPARATUS TO REDUCE ARTIFACTS IN A COMPUTED-TOMOGRAPHY (CT) IMAGE BY ITERATIVE RECONSTRUCTION (IR) USING A COST FUNCTION WITH A DE-EMPHASIS OPERATOR

CROSS-REFERENCE TO RELATED APPLICATIONS

This application is based upon and claims the benefit of priority to provisional U.S. Application No. 62/581,465, filed Nov. 3, 2017, the entire contents of which are incorporated herein by reference.

FIELD

The illustrative embodiments described herein relate to suppressing artifacts in images reconstructed by computed tomography (CT), and, more particularly, to reducing artifacts due to X-ray attenuation at one or more projection angles by an object outside of the field of view of the reconstructed image, the reduction in the artifacts attributable to an iterative reconstruction method that de-emphasizes attenuation due to objects outside the FOV, especially high-contrast objects.

BACKGROUND

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region (i.e., an X-ray projection plane) defining a cross-sectional slice of the body. At least one detector (and generally many more than one detector) on the opposite side of the body receives radiation transmitted through the body substantially in the projection plane. The attenuation of the radiation that has passed through the body is measured by processing electrical signals received from the detector.

Making projective measurements at a series of different projection angles through the body, a sinogram can be constructed from the projection data, with the spatial dimension of the detector array along one axis (e.g., the vertical axis) and the projection angle dimension along the other axis (e.g., the horizontal axis). The attenuation resulting from a particular volume with the body (e.g., a vertebra) will trace out a sine wave for the spatial dimension along the detector perpendicular to the rotation axis of the CT system. Volumes of the body farther from the center of rotation correspond to sine waves with greater amplitudes than those corresponding to volumes nearer the center of rotation. The phase of each sine wave in the sinogram corresponds to the relative angular positions with respect to the rotation axis. Performing an inverse Radon transform (or an equivalent image reconstruction method) reconstructs an image from the projection data in the sinogram, where the reconstructed image corresponding to a cross-sectional slice of the body.

The projection data is used for image reconstruction. Having obtained and corrected the projection data for measurement and detector artifacts, the projection data is prepared to reconstruct an image of an object OBJ. Generally, the image reconstruction problem can be solved using any of several methods including: back-projection methods (e.g., filtered back-projection), iterative reconstruction methods (e.g., the algebraic reconstruction technique (ART) method and the total variation minimization regularization methods), Fourier-transform-based methods (e.g., direct Fourier method), and statistical methods (e.g., maximum-likelihood expectation-maximization algorithm based methods).

Often the image reconstruction problem will be formulated as a matrix equation $$Ax=p,$$

where p are the projection measurements of the X-rays transmitted through an object space that includes the object OBJ, A is the system matrix describing the discretized line integrals (i.e., the Radon transforms) of the X-rays through the object space, and x is the image of object OBJ (i.e., the quantity to be solved for by solving the system matrix equation). The image x is a map of the attenuation as a function of position. The image x can be reconstructed from the projection data p using one of many reconstruction methods, including, a filtered-back-projection (FBP) method, a Feldkamp-Davis-Kress (FDK) method, and an iterative reconstruction (IR) method. Unfortunately, reconstructed image can include artifacts degrading the image when the projections include attenuation from objects located outside of the field of view (FOV) of the reconstructed image. For example, the artifacts can be especially significant when the outside objects are highly attenuating, such as in an interventional procedure in which all or part of a medical device is located outside the FOV but in the path of the X-rays and the medical device includes metal parts.

The above situation is not uncommon. For example, C-arm cone-beam computed tomography (CBCT) has been used increasingly as an imaging tool in surgical suites. CBCT has the benefit of rapidly providing detailed 3D anatomical information. Further, CBCT can also be used generate images with high spatial resolution, and, therefore, C-arm CBCT has been widely used in numerous imaging applications of high-contrast structures such as the sinuses, teeth, spines and contrast-enhanced vasculatures. However, in conventional analytical image reconstruction, soft-tissue imaging using C-arm CBCT remains challenging due to relatively poor low-contrast detectability of the detectors and high levels of noise and artifacts. Further, conventional CBCT systems have a limited field of view (FOV), and, therefore, current clinical C-arm CBCT often suffers from truncation artifacts, for the reason discussed above. Commonly, this limited field of view (FOV) results in a situation during an interventional procedure that a medical device or wire is in the X-ray path but outside the FOV, resulting in strong attenuation and compounding the artifacts due to truncation.

BRIEF DESCRIPTION OF THE DRAWINGS

A more complete appreciation of the disclosed inventions and the many attendant advantages thereof will be readily obtained as the same becomes better understood by reference to the following detailed description when considered in connection with the accompanying drawings, wherein.

DETAILED DESCRIPTION

Figure 1:
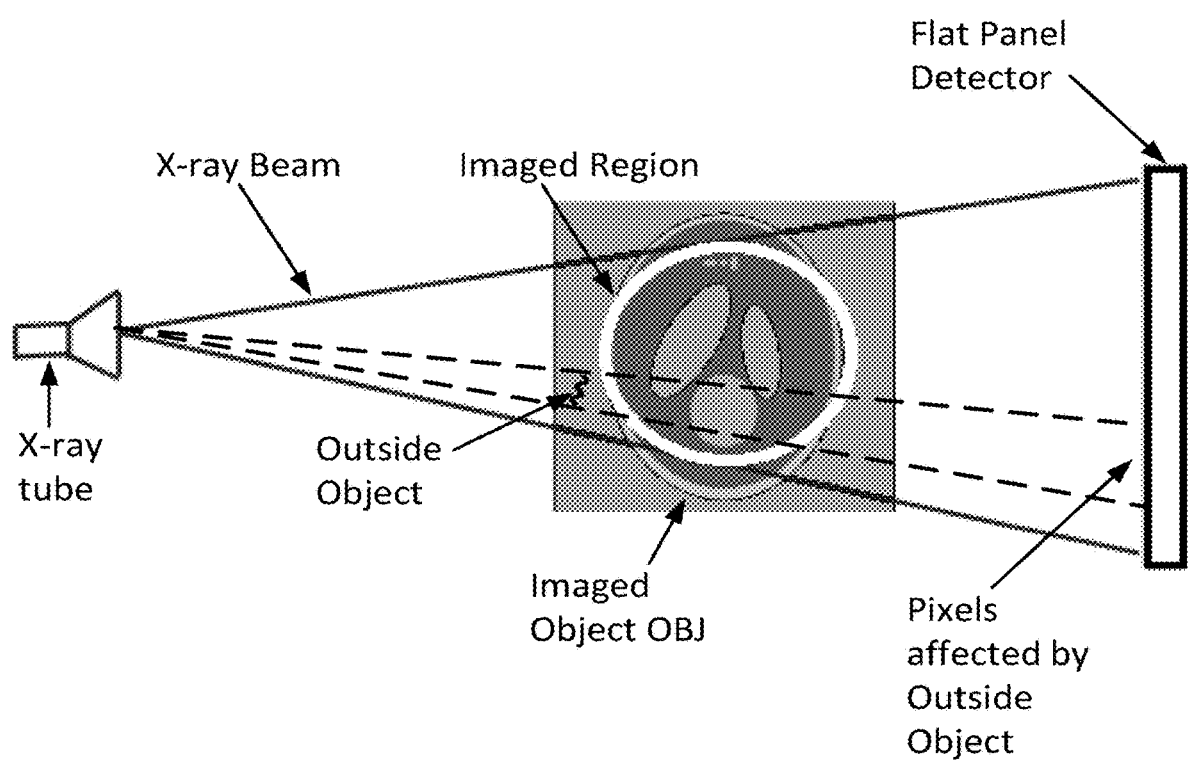
FIG. 1 shows a diagram of a computed tomography (CT)-scanner in which truncation artifacts arise due to both the imaged object being smaller than the field of view (FOV) of the reconstructed image and an outside object, such as a wire or medical device, being outside of the FOV, according to one implementation.

The methods and apparatus described herein reduce the above-discussed artifacts arising from outside objects (outside objects are those objects that are outside the field of view (FOV) of a reconstructed image). These artifacts are suppressed, for example, by using an iterative reconstruction (IR) method to minimize a cost function that includes a de-emphasis operator that de-emphasizes or otherwise filter out the attenuation due to the outside objects (e.g., by penalizing image solutions exhibiting features/artifacts corresponding to attenuation by outside objects or by de-emphasizing pixel values of the projection data corresponding to inconsistencies in the projection data caused by outside objects). This method and its consequent suppression of artifacts are beneficial for many applications including monitoring interventional and surgical procedures.

C-arm cone-beam CT (CBCT) is increasingly being used for imaging and guidance during interventional and surgical procedures. However, measured CBCT data are truncated often due to the limited detector size especially in the presence of additional interventional devices outside the imaging field of view (FOV). To remedy these problems, the methods described herein use optimization-based image reconstruction to reduce truncation artifacts commonly observed in clinical reconstructions. In certain implementations, the reconstruction problem is formulated as a constrained optimization program in which a de-emphasis operator suppresses artifacts in the solution of the constrained optimization. In certain implementations, the reconstruction problem is formulated as a constrained optimization program in which the de-emphasis operator includes a data-derivative fidelity term to suppress the truncation artifacts. Further, in certain implementations, a Chambolle-Pock (CP) algorithm is applied to solving the optimization program.

The following non-limiting example illustrates how the above-discussed artifacts arise in the application of C-arm CBCT to three-dimensional (3D) low contrast imaging (LCI). In 3D-LCI acquisitions, a 3D image (i.e., volume pixel data, also referred to as voxels) is generated for doctors to monitor conditions of patients and make follow-up checks and diagnoses of patients. To accommodate these uses, the C-arm system is often mobile and can perform 3D scans in flexible positions and orientations. Because of these advantageous attributes, 3D-LCI is often used in interventional procedure such as neuroradiology interventional procedures.

In these procedures, high-contrast objects such as metal devices, patient monitor wires, guide wires, and catheters can be used. During the procedure, these devices and wires can be variously positioned in and around the patient's body within the path of the X-ray radiation but outside of the FOV of the reconstructed image. Because high-density objects such as medical devices can cause X-ray photon starvation and beam hardening effects, those pixels of the projection data corresponding to ray trajectories through a metal device might not be salvageable/recoverable through beam-hardening or other corrections. Consequently, these unrecoverable pixels might not accurately represent the attenuation along their respective ray trajectories, and, therefore, their contribution to reconstructing an image might introduce artifacts and degrade the reconstructed image. That is, these pixels tended to create a data inconsistency for the 3D image reconstruction.

Referring now to the drawings, wherein like reference numerals designate identical or corresponding parts throughout the several views, FIG. 1 shows a diagram of an X-ray projection system with a flat panel detector (FPD). In this diagram the imaged region is smaller than the imaged object OBJ and an outside object is arranged outside the imaged region (i.e., the FOV of the reconstructed image). As shown in FIG. 1, a projection image is acquired using a small FPD. Thus, the imaged object OBJ is larger than the imaged region, which is shown as a white circle superimposed on imaged object OBJ. Using a small image volume creates a potential for truncation artifacts in a reconstructed image due to the attenuation of the projection data arising from portions of the object OBJ outside of the imaged region. The smaller size of the FDP can result in data truncation during data acquisition for three-dimensional reconstruction.

For some projection angles, the acquisition FOV fails to completely span the object OBJ, such that data that would make it possible to perfectly characterize the object OBJ is missing due to the limited extent of the FDP. The missed data will reduce the amount of known projection data p available to reconstruct the image based on the system-matrix equation $Ax \approx p$ (e.g., IR algorithms can be understood as iterative algorithms to solve this system-matrix equation). When the FOV includes less than the entire object OBJ, the system-matrix equation tends to be underdetermined. That is, as a result of the system-matrix being modeled using a forward projection A, the image inside the FOV is more constrained by the equations than the image outside FOV, resulting in artifacts in the reconstructed image.

Further, artifacts will be generated due to the outside object (e.g., a wire, catheter, or medical device) that is also outside of the FOV, and these artifacts can be especially detrimental to the image quality of the reconstructed image because the outside object often strongly attenuates the X-rays, as described above. The dashed lines show the trajectories of X-rays passing through the outside object, and the pixels of the FPD corresponding to these trajectories are the pixels affected by the outside object. De-emphasizing these affected pixels or otherwise filtering out or penalizing image solutions representing the attenuation due to the outside object will suppress the artifacts due to the outside object. And this is variously achieved by the IR method using the types of de-emphasis operators described herein.

When the metal devices or wires are within the FOV, certain methods can be used to reduce the artifacts arising therefrom, but these methods are not available when the metal devices or wires are outside the FOV. For example, for high-density objects inside the FOV metal artifact reduction algorithms can be used. In certain implementations, metal artifact reduction for inside objects (i.e., high contrasts objects inside the FOV) is achieved by, in the image domain, segmenting the metal image and replacing the metal regions in the projection domain with a more accurate projection data using interpolation and re-projection of the reconstructed 3D image. A more detailed description of a metal artifact reduction algorithm is provided in U.S. patent application Ser. No. 14/746,012, incorporated herein by reference in its entirety. In contrast to the above segmentation method in the image domain, the de-emphasis operators described herein operate in the data domain (also referred to as the sinogram domain or the domain of the projection data).

Additionally, pre-reconstruction data processing such as data extrapolation can be used to partially address the truncation issue, but pre-reconstruction data processing is not completely effective and can introduce other artifacts. That is, while some pre-reconstruction data processing may help reduce data truncation artifacts in some situations, it can introduce additional artifacts due to the inadequate data estimation, especially when some high-contrast interventional devices outside the imaging FOV are present. In contrast to pre-reconstruction data processing, the de-emphasis operators described herein operate during the image reconstruction.

To improve artifact suppression, the methods described herein use optimization-based reconstruction to compensate for data-degrading factors, including data truncation. These optimization-based reconstruction methods are demonstrated to reduce image artifacts observed in clinical reconstructions when applied to reconstruction CT images from truncated data. This achievement is achieved, e.g., by formulating the reconstruction problem as a constrained optimization program in which a de-emphasis operator is used to suppress the truncation artifacts.

Figure 2A:
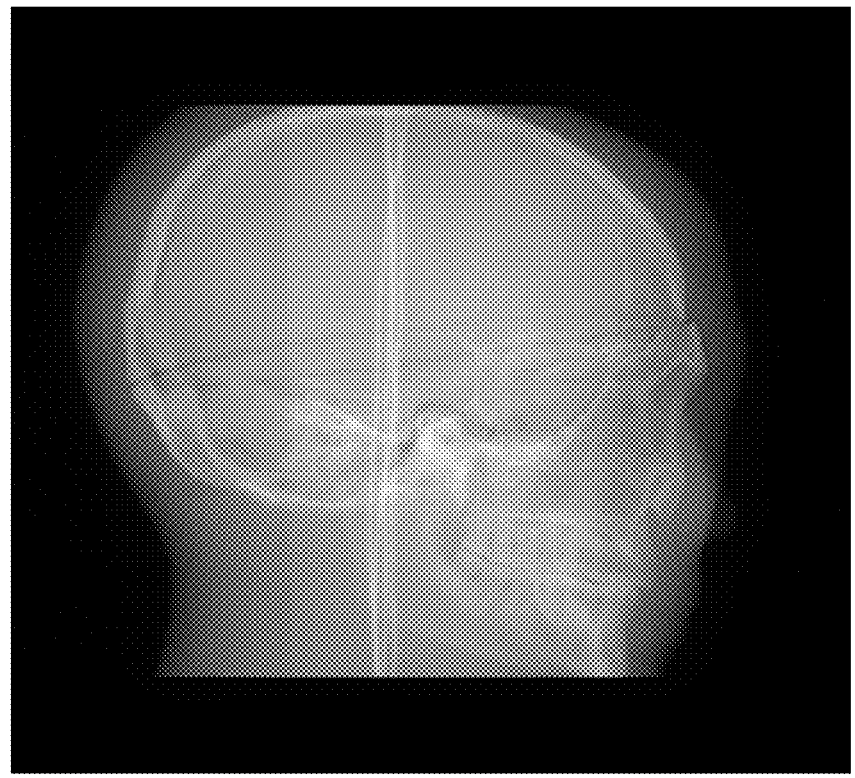
FIG. 2A shows a projection image of a head phantom, according to one projection angle for which an outside object is in the X-ray path.
Figure 2B:
FIG. 2B shows a projection image of the head phantom, according to another projection angle for which the outside object is not in the X-ray path.

FIGS. 2A and 2B illustrate projection images of the projection at two different angles. In the view (i.e. projection angle) shown in FIG. 2A shows a view in which some trajectories pass through a high-contrast object outside of the FOV of the reconstructed image. For the view shown in FIG. 2B none of the X-ray trajectories pass through the high-contrast outside object. If high-density objects are outside the FOV, they are partially imaged at a certain range of rotational angle. Accordingly, approaches for reducing metal artifacts that work when the metal is in the FOV are difficult to perform. For example, reconstructing metal images of the outside object might be difficult, preventing segmentation and re-projection of the metal image because the high-density outside objects can, at best, be only partially reconstructed from insufficient frames. Thus, a new metal artifact reduction algorithm is desirable because methods based on reconstructing an image of outside object and then forward projecting the reconstructed image to identify the metal projection are insufficient.

Figure 3A:
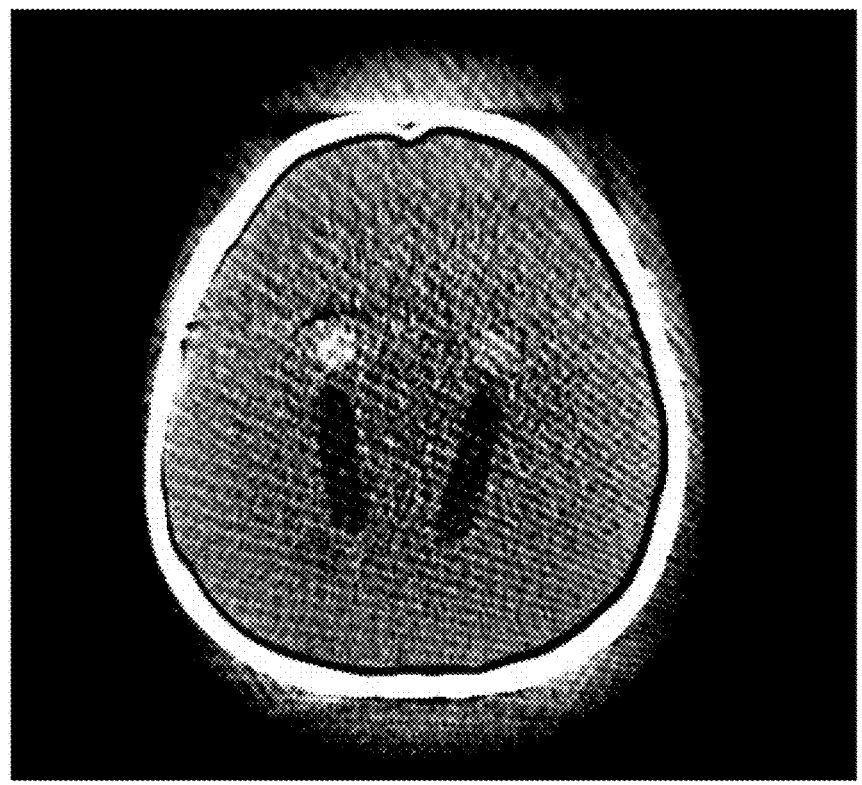
FIG. 3A shows a first cross-section of an image reconstructed using a Feldkamp-Davis-Kress (FDK) algorithm, according to one implementation.
Figure 3B:
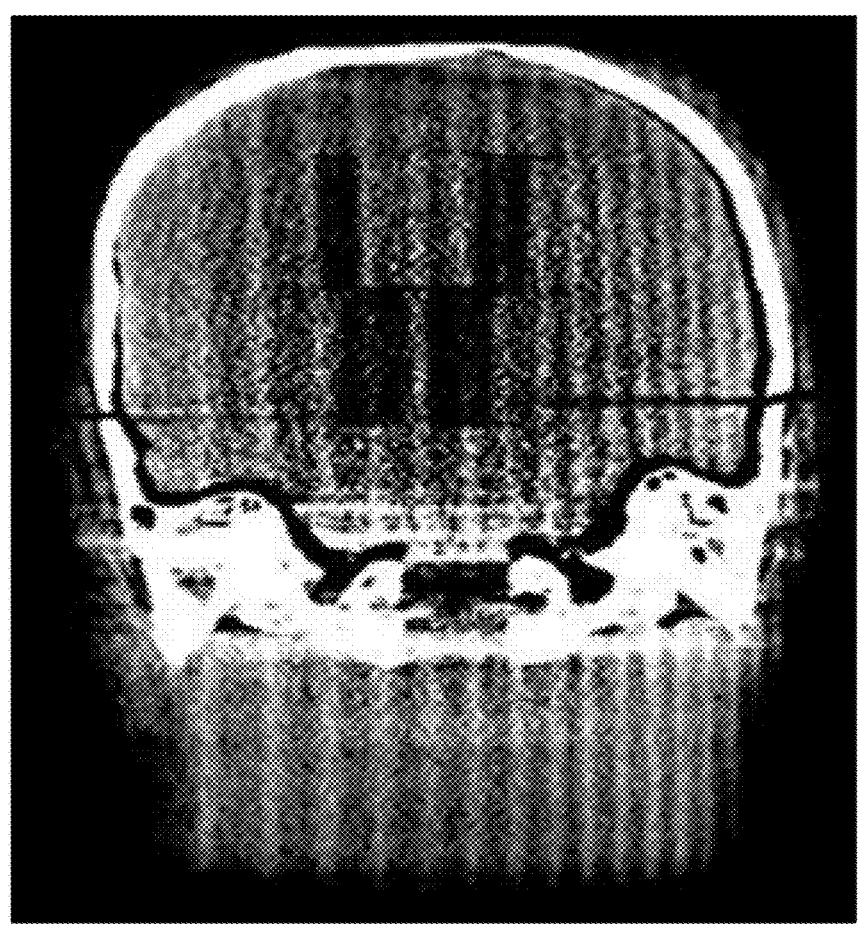
FIG. 3B shows a second cross-section of the image reconstructed using the FDK algorithm, according to one implementation.
Figure 3C:
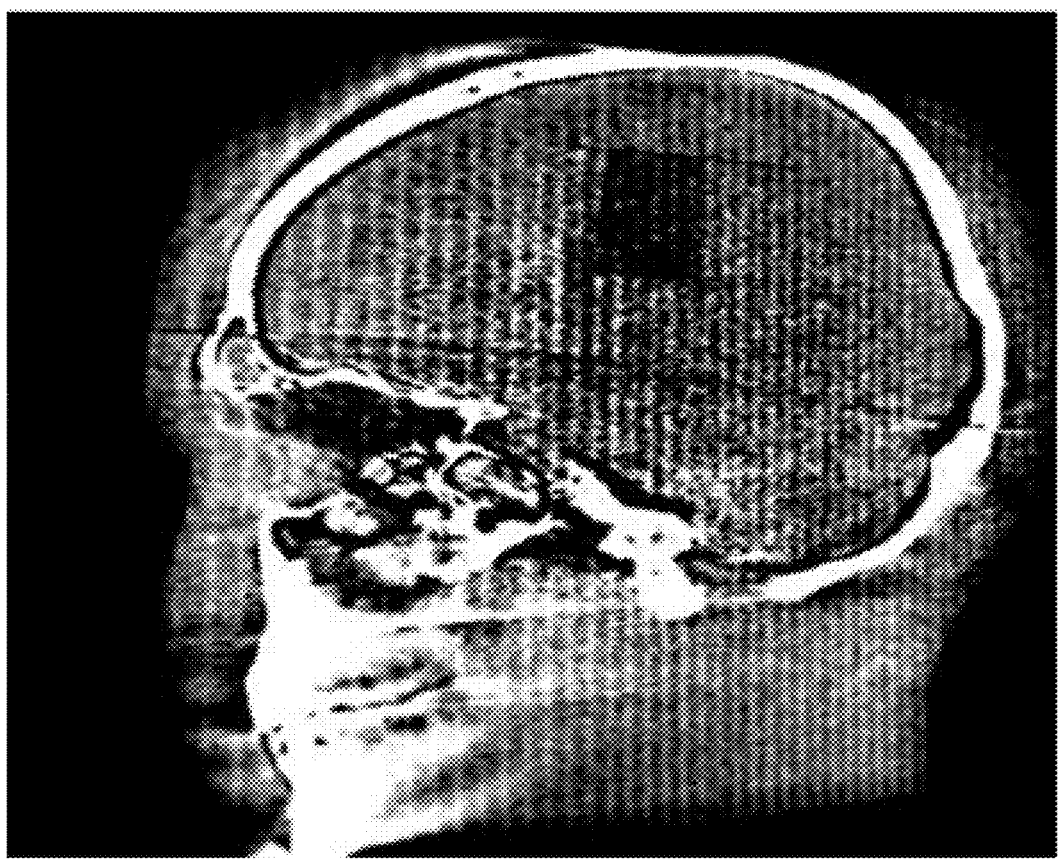
FIG. 3C shows a third cross-section of the image reconstructed using the FDK algorithm, according to one implementation.

The problem of outside objects is illustrated in FIGS. 2A and 2B, in which a wire is placed at the side of the phantom so that the wire is scanned at a projection angle of −60 degrees (shown in FIG. 2A), but the wire is completely outside the X-ray beam trajectories at a projection angle of 0 degrees (shown in FIG. 2B). FIGS. 3A, 3B, and 3C show that, using conventional reconstruction methods image, the outside object results in streak artifacts in the reconstructed image. FIGS. 3A, 3B, and 3C respectively show three orthogonal cross-sections of a 3D image that was reconstructed, using an FDK algorithm, from projection data that includes the projection images shown in FIGS. 2A and 2B.

The streak artifacts are reduced using a reconstruction method that includes an operator to de-emphasize in the projection domain the projection data representing an inconsistency relative to the remaining projection data (e.g., pixels corresponding to the outside object). For example, the proposed solution to reduce the artifacts due to outside objects is to reconstruct the image using an iterative reconstruction algorithm that applies a de-emphasis operator in the data domain. In certain implementations, the cost function for the iterative reconstruction algorithm is expressed as $$f(x)=f_{IR}(x)+\|D(Ax-p)\|^2,$$

wherein D is an enhancement operator (also referred to a de-emphasis operator). The function of the de-emphasis operator D can be understood by considering that when there is data inconsistency in p (e.g., due to an outside object that affects a limited set of views/projection angles) minimizing a cost function that includes only a data fidelity term, $\|(Ax-p)\|^2$ results in streak artifacts in the image x (as shown in FIGS. 3A, 3B, and 3C). In the presence of significant data inconsistency in the projection domain, D is configured to favour convergence to a solution that de-emphasize data inconsistencies arising from high-density objects. For example, D can filter out data inconsistencies bearing indicia that they arise from an outside or high-contrast object, or by penalizing image solutions bearing indicia of artifacts arising from outside or high-contrast object. Thus, the reconstructed image x is robust to and effectively disregards those data inconsistencies arising from the outside object, with the effect that the reconstructed image derives from attenuation due to the object inside the FOV and therefore represents the object inside the FOV with outside attenuation suppressed.

As discussed above, in certain implementations, an unconstrained cost function is used for iterative reconstruction with de-emphasis operator $$f(x)=f_{IR}(x)+\lambda\|D(Ax-p)\|^2,$$

wherein $f_{IR}(x)$ is an unconstrained cost function of iterative reconstruction (any known cost function including, e.g., any known data fidelity term and/or regularization terms), λ is a weighting factor to balance the relative contributions between the term $f_{IR}(x)$ and the de-emphasis term, x is an image to be solved for by iterative updates to search for a minimum of the cost function, A is system matrix which models interaction of x-ray beam with scanned objects, p is acquired projection data (e.g., from C-arm CBCT scanner). The unconstrained cost function $\eta_{IR}(x)$ can be, e.g., an objective function that includes a least-squares or a penalized-weighted-least-squares data-fidelity term and a regularization term. The optimization problem can be expressed as $$\tilde{x}=\min f(x).$$

Figure 4:
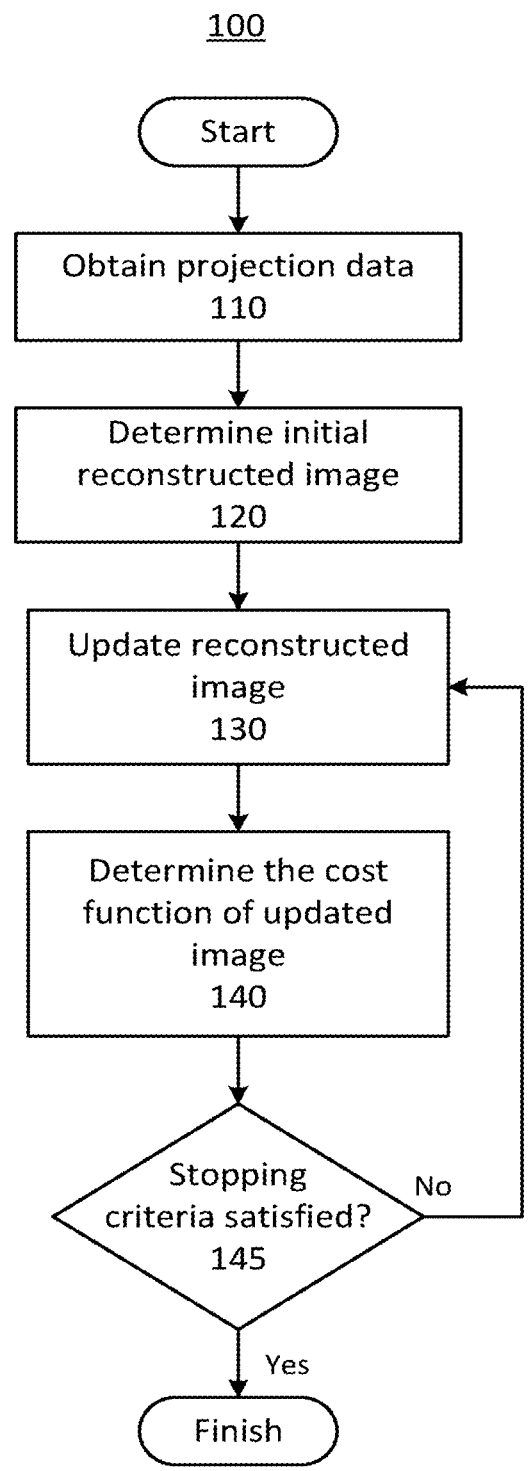
FIG. 4 shows a flow diagram of a method of reconstructing a CT image while suppressing artifacts due to outside objects (i.e., outside the FOV), according to one implementation.

FIG. 4 shows a method 100 of generating a reconstructed image x using an IR method with a de-emphasis operator.

In step 110, the projection data is obtained. This projection data can be obtained by performing a CT scan using a CT scanner such as the CT scanner described herein. Also, the projection data can be obtained by recalling from computer memory projection data that has been previously obtained.

In the non-limiting example shown in FIGS. 2A and 2B, the projection data was collected with a C-arm system (Toshiba Infinix-i™), with an X-ray source and a flat-panel detector mounted onto the opposing ends of the C-arm. The distances from X-ray source to the rotation center and to the detector are 700 mm and 1100 mm, respectively. The flat-panel detector consists of a 1024×1024 array with a 0.29 mm pitch (rebinned to an 512×512 array with a bin size of 0.58×0.58 mm), forming a FOV of size 18.7 cm, which might be insufficient to cover the entire transverse cross section of a scanned subject. For example, the FOV might be too small to cover all attenuating objects especially when injection-devices and/or contrast objects are present outside the body contour, leading to streak artifacts in clinical images as discussed above. Such artifacts may obscure low-contrast soft-tissue anatomy in the applications of clinical interest (e.g., intracranial hemorrhages might be obscured by the streak artifacts). The projection data in FIGS. 2A and 2B was obtained using a C-arm CBCT data scan of a physical head phantom. Prior to reconstruction using the projection data in FIGS. 2A and 2B, scatter correction and beam-hardening correction were performed.

In step 120 of method 100, an initial reconstructed image can be determined. Preferably the initial image is generated using a method that is fast and uses relatively little computational resources. For example, the initial image can be generated using downsampled projection data and using an image resolution for the initial image that is commensurate with the downsampled projection data. The initial image can be a defaults image, or can be generated using any known CT reconstruction method, including filtered back-projection (FBP), a Feldkamp-Davis-Kress (FDK) reconstruction method, and an IR method using (although not necessarily to convergence). In certain implementations using an IR method, the IR method can be performed for a predefined number of iterations, rather than being performed until convergence, and the IR method can use acceleration methods such as ordered subsets (OS), separable quadratic surrogate (SQS), and Nesterov's momentum acceleration. Further, the initial reconstructed image can be generated using a combination of IR methods and FBP or FDK methods (e.g., the IR method can be initialized using a FBP or FDK reconstructed image). Accordingly, various combinations of CT reconstruction can be used, as would be understood by a person of ordinary skill in the art.

In one non-limiting example, FIGS. 3A, 3B, and 3C were reconstructed from the projection data illustrated in FIGS. 2A and 2B using an FDK algorithm. The image arrays of sizes N=700×560×512 were used for the physical head phantom, in which the voxel size is 0.47 mm.

In step 130 of method 100, the image x is updated. The updated image x is generated using the cost function that includes the de-emphasis operator D in the projection domain (also referred to as the data domain as opposed to the image domain), as discussed above. The de-emphasis operator D can take various forms, depending on the implementation.

For example, in certain implementations, it can be assumed that, in the data domain, spatial changes in attenuation are smooth. This is the case for a low-contrast image, such as for the head phantom shown in FIGS. 2A and 2B. Thus, the data consistency can be suppressed by penalizing solutions corresponding to sharp spatial changes in the data domain, especially sharp changes data inconsistency as expressed in the difference between the forward projection of the image and the projection data (i.e., Ax−p).

Accordingly, in certain implementations, the de-emphasis operator D is realized by performing an operation of edge and sharpness enhancement to Ax−p to enhance boundaries of a high-density object region in Ax−p, and then the region of high-density object region in Ax−p is de-emphasized by using the result of the edge and sharpness enhancement to Ax−p to penalize an image for which is data inconsistency has sharp spatial edges/features. For example, sharp spatial edges/features in the data domain can be indicia of streak artifacts due to high-contrast objects outside the FOV.

Additionally, in certain implementations, the de-emphasis operator D performs operation of high-pass filter to the data-inconsistency term Ax−p, and the result is used to penalize solutions with significant high-frequency content in the data-inconsistency term.

Further, in certain implementations, the de-emphasis operator D includes a first-order derivative to the data-inconsistency term Ax−p, and the result is used to penalize solutions with large first-order derivatives in the data-inconsistency term.

In some the above examples, the attenuation due to the outside object has been effectively de-emphasized, albeit indirectly, by emphasizing/penalizing the indicia of artifacts arising from the attenuation due to the outside object. Thus, in certain implementations, the de-emphasis operator has the effect of de-emphasizing the attenuation due to the outside object relative to the attenuation arising from objects inside the FOV, even if the de-emphasis operator does not operate directly to decrease, in the data-inconsistency term, those components of the attenuation attributable to the outside object. Nevertheless, a same objective is achieved (e.g., making the reconstructed image in the FOV robust against outside objects), whether the de-emphasis operator acts on the data-inconsistency to reduce components attributable to the outside object or the de-emphasis operator acts on the data-inconsistency to penalize images exhibiting indicia of artifacts attributable to the outside object (e.g., the sharp edges and high-frequency content of the streak artifacts).

To complete the iterative reconstruction method, the image x is iteratively updated and the convergence of the updated image x is monitored according to some stopping criteria. In the non-limiting example of method 100, this is achieved using steps 140 and 145. In step 140, the cost function of the updated image x is calculated. Then in step 145 the stopping criteria are evaluated. If the stopping criteria have not been satisfied, method 100 proceeds from step 145 to step 130 and the iterative loop beginning from step 130 and continuing through step 140 is repeated. Otherwise, method 100 is complete. The stopping criteria can include for example a convergence criterion (e.g., based on a difference between successive iterations of the image x) and a criterion for a maximum number of iterations.

Figure 5A:
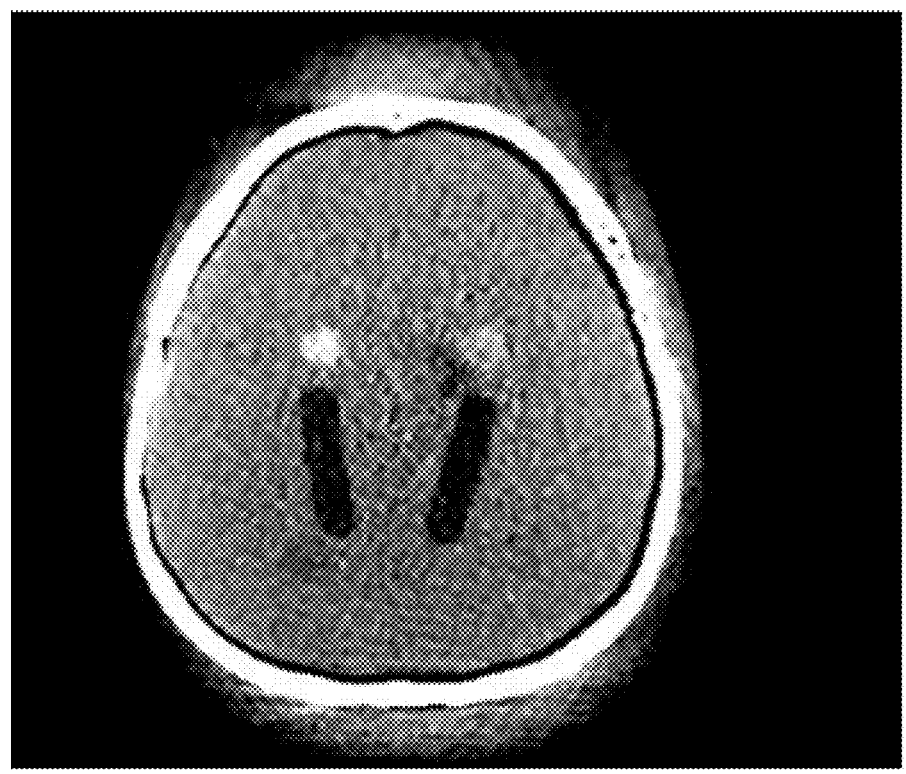
FIG. 5A shows a first cross-section of an image reconstructed using an iterative reconstruction (IR) method with a de-emphasis operator, according to one implementation.
Figure 5B:
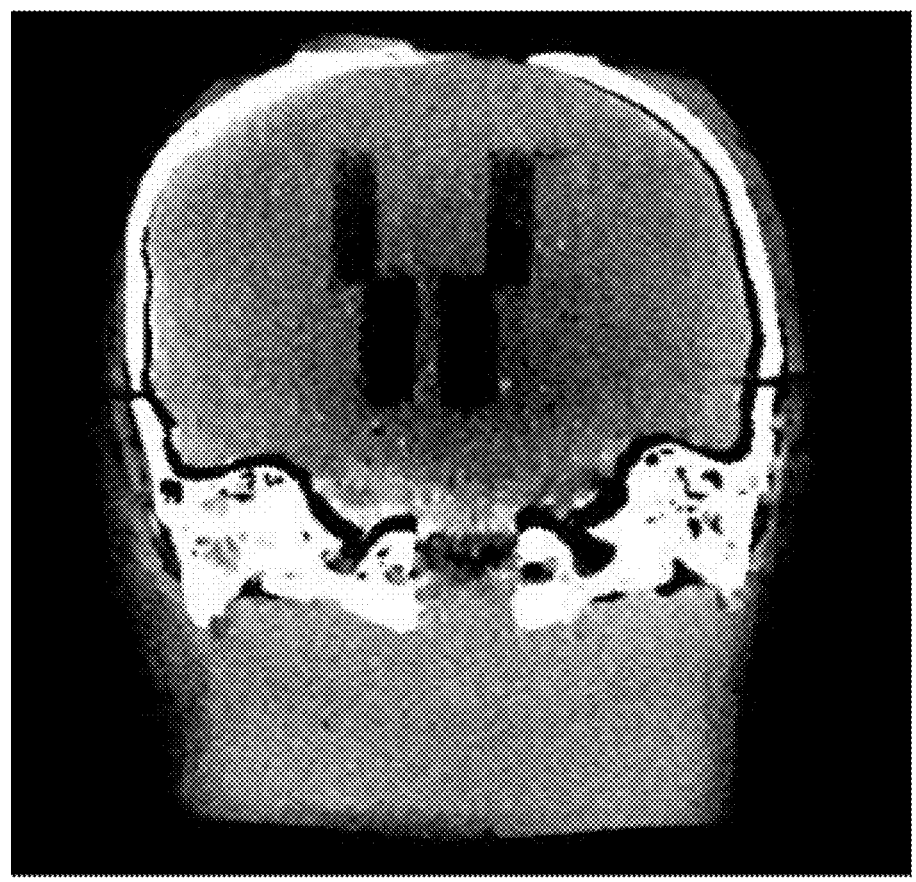
FIG. 5B shows a second cross-section of the image reconstructed using the IR method with the de-emphasis operator, according to one implementation.
Figure 5C:
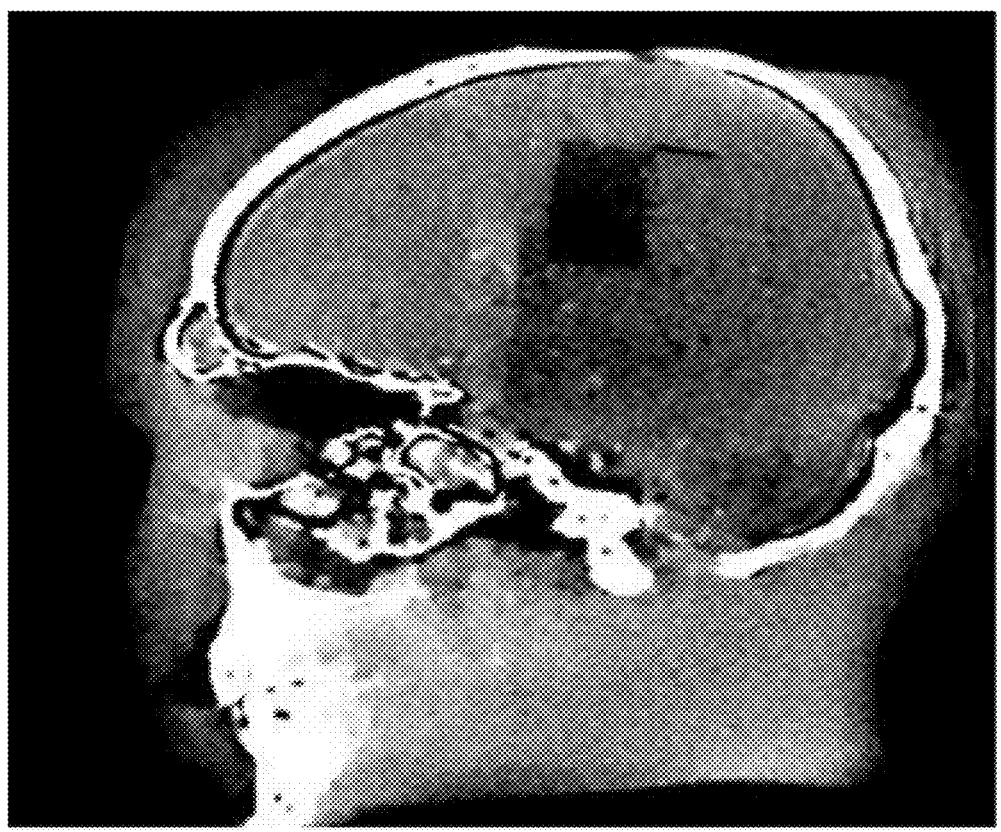
FIG. 5C shows a third cross-section of the image reconstructed using the IR method with the de-emphasis operator, according to one implementation.

For example, the reconstructed images in FIGS. 5A, 5B, and 5C were obtained by iteratively reconstructing a cost function that includes a de-emphasis operator. FIGS. 5A, 5B, and 5C show cross-section respectively corresponding to FIGS. 3A, 3B, and 3C. Comparing FIGS. 5A, 5B, and 5C with FIGS. 3A, 3B, and 3C demonstrates that, whereas severe streak artifacts in the FDK reconstruction obscure the low-contrast objects in the phantom, the reconstruction method used in FIGS. 5A, 5B, and 5C suppresses the streak artifacts and the low-contrast objects can be easily identified.

When the sinogram of the projection data is displayed with projection angle along the horizontal axis and the detector direction perpendicular to the projection axis along the vertical axis, attenuation due to the object inside the FOV will correspond to sinusoids along the horizontal axis for which the maximum amplitude is limited by the radius of the FOV. The sinusoids corresponding to objects outside the FOV will have amplitudes greater than this maximum corresponding to the FOV. One consequence of these large amplitudes is that the slope of the sinusoid around the isocenter will be greater for outside objects than objects inside the FOV. Thus, by considering the data-inconsistency term Ax−p as a sinogram, the de-emphasis operator can selectively minimize sinusoid components corresponding to amplitudes greater than the maximum sinusoid amplitude within the FOV. Alternatively, the de-emphasis operator can selectively minimize linear components having slopes around the isocenter (i.e., the slope being change in horizontal pixel position as a function of projection angle) greater than the maximum slope for the maximum sinusoid amplitude within the FOV In general, the cost function including the de-emphasis operator D can be minimized using any known iterative method to solve for the reconstructed image x. Examples of iterative methods for minimizing a cost function include, but are not limited to, gradient descent methods, OS methods, SQS methods, Nesterov's momentum acceleration methods, and combinations therefore. And these can include various corrections, including, e.g., scatter and beam hardening corrections. As mentioned above the cost function can include terms such as a data-derivative term (or other variation of de-emphasis operator), a data-divergence term (also referred to as data fidelity term), and a regularization term (or a regularization constraint).

When the matrix equation is cast as an optimization problem, any of a number of iterative algorithms can be used to solve the optimization problem. For example, the algebraic reconstruction technique (ART) uses an iterative method of affine projections by refining estimates of the image x through a succession of projections onto each of the affine spaces defined by the rows of the system matrix equation. Performing this series of affine projections and then repeating them again and again causes the image estimate to converge to a solution of the system matrix equation. Interjecting a regularization condition/term between series of affine projections imposes constraints on the solution, and ensures that the reconstructed image converges to a physically meaningful and realistic solution. For example, bodies are known to absorb radiation, making gain through a body (i.e., negative attenuation) an unphysical result. Therefore, a non-negative regularization condition can be imposed to eliminate unphysical gain regions in the reconstructed image.

Iterative reconstruction algorithms augmented with regularization conditions can produce high-quality reconstructions using only a few views even in the presence of significant noise. For few-view, limited-angle, and noisy projection scenarios, the application of regularization operators between reconstruction iterations seeks to tune the final result to be consistent with a certain a priori model. For example, enforcing positivity, as discussed above, is a simple but common regularization scheme.

A second regularization condition is total variation (TV) minimization in conjunction with projection on convex sets (POCS). The TV-minimization algorithm assumes that the image is predominantly uniform over large regions with sharp transitions at the boundaries of the uniform regions. When the a priori model corresponds well to the image object, these regularized iterative reconstruction algorithms can produce impressive images even though the reconstruction problem is significantly underdetermined (e.g., the few-view scenario), missing projection angles, or the data is noisy. The optimization problem with TV regularization can be expressed as $$\operatorname*{argmin}_{x}\left\{\frac{1}{2}\|Ax-p\|_{2}^{2}+\lambda\|(|\nabla x|)\|_{1}\right\},$$

wherein the last term, the $l_1$-norm of the gradient-magnitude image, is the isotropic TV semi-norm. The spatial-vector image $\nabla x$ represents a discrete approximation to the image gradient. The expression $|\nabla x|$ is the gradient-magnitude image, an image array whose pixel values are the gradient magnitude at the pixel location.

Having formulated the optimization problem, there are many choices of algorithms for solving the optimization problem, some of which are more efficient than others, depending on the details of the optimization problem. For example, the dual-primal Chambolle-Pock (CP) algorithm can be efficient for solving certain image reconstruction optimization problems.

Two other related methods for iteratively solving optimization problems are the alternating direction method of multipliers (ADMM) and the augmented Lagrangian multiplier methods. These two methods are examples of splitting-based iterative algorithms. These splitting-based iterative methods exhibit the efficiencies introduced by subdividing a single optimization problem into a series of subproblems that can be solved in an iterative manner.

Although it can be developed in a slightly more general form, the following problem formulation is sufficient for most applications of the ADMM:

$$\min_{x \subset^n} f(x) + g(Mx)$$

where, M is an m×n matrix, often assumed to have full column rank, and $f$ and g are convex functions on $i^n$ and $i^m$, respectively. In addition to values in, the functions $f$ and g can also have the value $+\infty$, so that constraints may be "embedded" in $f$ and g, in the sense that if $f(x)=\infty$ or $g(Mx)=\infty$, then the point x is considered to be infeasible.

By appropriate use of infinite values for $f$ or g, a very wide range of convex problems may be modeled by this optimization problem. To make the discussion more concrete, however, herein is described a simple illustrative example that fits very readily into this form without any use of infinite function values, and resembles in basic structure many of applications responsible for the resurgence of interest in the ADMM: the "lasso" or "compressed sensing" problem. This problem takes the form $$\min_{x \in i^m} \frac{1}{2}\|Ax-b\|^2 + v\|x\|_1,$$

where A is a p×n matrix, $b \in i^p$, and $v > 0$ is a given scalar parameter. The idea of the model is find an approximate solution to the linear equations Ax=b, but with a preference for making the solution vector x∈i$^n$ sparse; the larger the value of the parameter v, the more the model prefers sparsity of the solution versus accuracy of solving Ax=b. While this model clearly has limitations in terms of finding sparse near-solutions to Ax=b, it serves as a good example application of the ADMM; many other now-popular applications have a similar general form, but may use more complicated norms in place $\|\cdot\|_1$; for example, in some applications, x is treated as a matrix, and one uses the nuclear norm (the sum of singular values) in the objective to try to induce x to have low rank.

Now, the classical augmented Lagrangian method and the ADMM are described for this optimization problem. First, note that the optimization problem can be rewritten, introducing an additional decision variable z∈i$^m$ as $$\min f(x)+g(z)$$

$$\text{ST } Mx=z$$

The classical augmented Lagrangian algorithm, is described in the case of the above formulation by the recursions $$(x^{k+1}, z^{k+1}) \in \underset{x \in i^n, z \in i^m}{\operatorname{argmin}}\left\{f(x) + g(z) + \langle \lambda^k, Mx - z \rangle + \frac{c_k}{2}\|Mx - z\|^2\right\}$$

$$\lambda^{k+1} = \lambda^k + c_k(Mx^{k+1} - z^{k+1}).$$

where, $\{\lambda^k\}$ is a sequence of estimates of the Lagrange multipliers of the constraints Mx=z, while $\{(x^k, z^k)\}$ is a sequence of estimates of the solution vectors x and z, and $\{c_k\}$ is a sequence of positive scalar parameters bounded away from 0. The notation <a,b> denotes the usual Euclidean inner product a$^T$b.

In this setting, the standard augmented Lagrangian algorithm is not very attractive because the minimizations of $f$ and g in the second subproblem in the above expression are strongly coupled through the term $$\frac{c_k}{2}\|Mx - z\|^2,$$

and hence the subproblems are not likely to be easier to solve than the original problem. In contrast, the alternating direction method of multipliers (ADMM) is formulated into subproblems that are easier to solve. The ADMM problem takes the form $$x^{k+1} \in \underset{x \in i^n}{\operatorname{argmin}}\left\{f(x) + g(z^k) + \langle \lambda^k, Mx - z^k \rangle + \frac{c}{2}\|Mx - z^k\|^2\right\}$$

$$z^{k+1} \in \underset{z \in i^m}{\operatorname{argmin}}\left\{f(x^{k+1}) + g(z) + \langle \lambda^k, Mx^{k+1} - z \rangle + \frac{c}{2}\|Mx^{k+1} - z\|^2\right\}$$

$$\lambda^{k+1} = \lambda^k + c(Mx^{k+1} - z^{k+1}).$$

Clearly, the constant terms $g(z^k)$ and $f(x^{k+1})$ as well as some other constants, may be dropped from the respective minimands in the above expressions. Unlike the classical augmented Lagrangian method, the ADMM essentially decouples the functions $f$ and g. In many situations, this decoupling makes it possible to exploit the individual structure of the $f$ and g so that the above expressions may be computed in an efficient and perhaps highly parallel manner.

Figure 6:
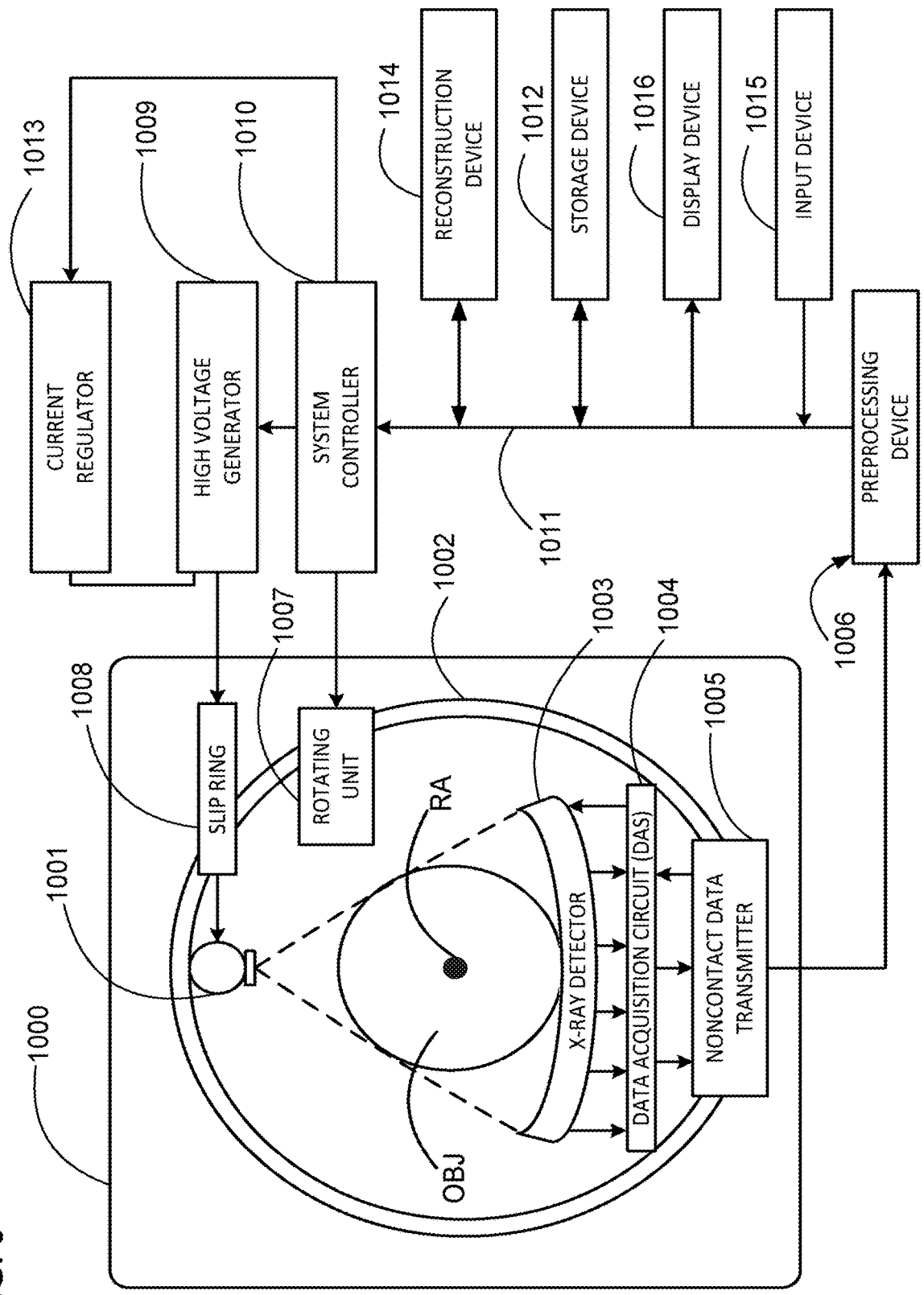
FIG. 6 shows a diagram of a CT scanner, according to one implementation.

FIG. 6 illustrates an implementation of the radiography gantry included in a CT apparatus or scanner. As shown in FIG. 6, a radiography gantry 1000 is illustrated from a side view and further includes an X-ray tube 1001, an annular frame 1002, and a multi-row or two-dimensional-array-type X-ray detector 1003. The X-ray tube 1001 and X-ray detector 1003 are diametrically mounted across an object OBJ on the annular frame 1002, which is rotatably supported around a rotation axis RA. A rotating unit 1007 rotates the annular frame 1002 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 1009 that generates a tube voltage applied to the X-ray tube 1001 through a slip ring 1008 so that the X-ray tube 1001 generates X-rays. The X-rays are emitted towards the object OBJ, whose cross sectional area is represented by a circle. For example, the X-ray tube 1001 having an average X-ray energy during a first scan that is less than an average X-ray energy during a second scan. Thus, two or more scans can be obtained corresponding to different X-ray energies. The X-ray detector 1003 is located at an opposite side from the X-ray tube 1001 across the object OBJ for detecting the emitted X-rays that have transmitted through the object OBJ. The X-ray detector 1003 further includes individual detector elements or units.

The CT apparatus further includes other devices for processing the detected signals from X-ray detector 1003. A data acquisition circuit or a Data Acquisition System (DAS) 1004 converts a signal output from the X-ray detector 1003 for each channel into a voltage signal, amplifies the signal, and further converts the signal into a digital signal. The X-ray detector 1003 and the DAS 1004 are configured to handle a predetermined total number of projections per rotation (TPPR).

The above-described data is sent to a preprocessing device 1006, which is housed in a console outside the radiography gantry 1000 through a non-contact data transmitter 1005. The preprocessing device 1006 performs certain corrections, such as sensitivity correction on the raw data. A memory 1012 stores the resultant data, which is also called projection data at a stage immediately before reconstruction processing. The memory 1012 is connected to a system controller 1010 through a data/control bus 1011, together with a reconstruction device 1014, input device 1015, and display 1016. The system controller 1010 controls a current regulator 1013 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1001 and the X-ray detector 1003 are diametrically mounted on the annular frame 1002 and are rotated around the object OBJ as the annular frame 1002 is rotated about the rotation axis RA. In the fourth-generation geometry system, the detectors are fixedly placed around the patient and an X-ray tube rotates around the patient. In an alternative embodiment, the radiography gantry 1000 has multiple detectors arranged on the annular frame 1002, which is supported by a C-arm and a stand.

The memory 1012 can store the measurement value representative of the irradiance of the X-rays at the X-ray detector unit 1003. Further, the memory 1012 can store a dedicated program for executing method 100.

The reconstruction device 1014 can execute method 100. Further, reconstruction device 1014 can execute pre-reconstruction processing image processing such as volume rendering processing and image difference processing as needed.

The pre-reconstruction processing of the projection data performed by the preprocessing device 1006 can include correcting for detector calibrations, detector nonlinearities, and polar effects, for example. Further, the pre-reconstruction processing can include various steps of method 100.

Post-reconstruction processing performed by the reconstruction device 1014 can include filtering and smoothing the image, volume rendering processing, and image difference processing as needed. The image reconstruction process can implement various steps of method 100. The reconstruction device 1014 can use the memory to store, e.g., projection data, reconstructed images, calibration data and parameters, and computer programs.

The reconstruction device 1014 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 1012 can be non-volatile, such as ROM, EPROM, EEPROM or FLASH memory. The memory 1012 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 1014 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1016. The display 1016 can be an LCD display, CRT display, plasma display, OLED, LED or any other display known in the art.

The memory 1012 can be a hard disk drive, CD-ROM drive, DVD drive, FLASH drive, RAM, ROM or any other electronic storage known in the art.

Figure 7:
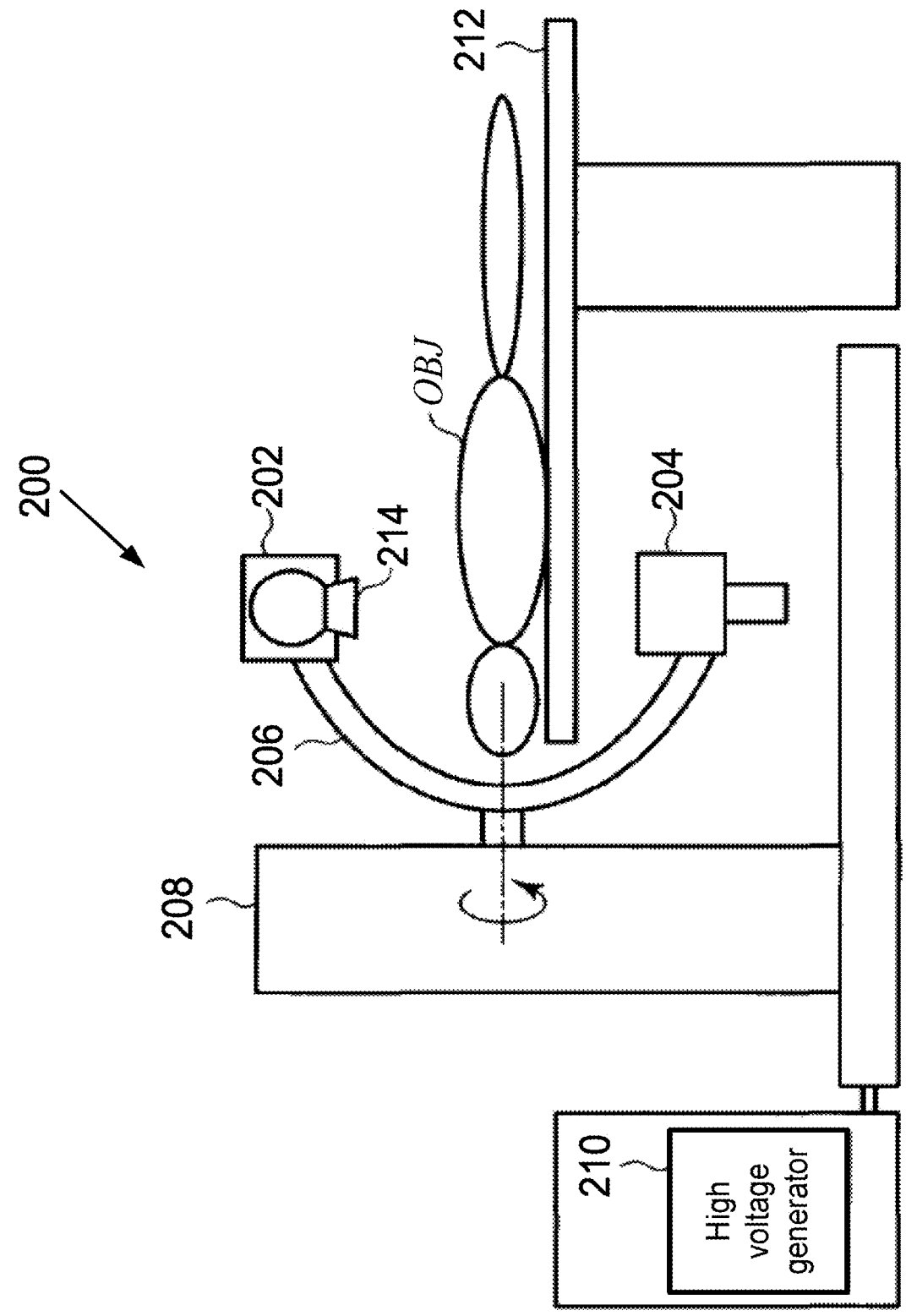
FIG. 7 shows a diagram of a C-arm CT scanner, according to one implementation.

FIG. 7 shows an example of a CT apparatus 100 or radiography gantry, wherein the apparatus uses a C-arm configuration. As shown in FIG. 7, the CT apparatus 200 includes an X-ray tube 202, X-ray detector 204, C-arm 206, stand 208, high-voltage generator 210, bed 212, and X-ray stop device 214.

The high-voltage generator 210 generates a high voltage to be applied between the electrodes of the X-ray tube 202, and also generates a filament current to be supplied to the cathode filament of the X-ray tube 202. Upon receiving the high voltage and filament current, the X-ray tube 202 generates X-rays. The X-ray stop device 214 shapes X-rays generated by the X-ray tube 202. The X-ray detector 204 can be a two-dimensional array of a plurality of detection elements (pixels) that directly or indirectly convert incident X-rays into electric charges. The X-ray tube 202 is mounted on, for example, one end of the floor type C-arm 306. The X-ray detector 204 is mounted on the other end of the C-arm 206. The X-ray detector 204 faces the X-ray tube 202 through an object OBJ to be examined which is placed on the bed 212. The C-arm 206 is rotatably supported on the stand 208. Repeating radiography with respect to the object OBJ while rotating the C-arm 206 makes it possible to acquire X-ray frames (projection data) in many directions which are required for three-dimensional image reconstruction.

Radiography control circuitry controls the rotation of the C-arm 206, the application of high voltages from the high-voltage generator 210 to the X-ray tube 202, and reading of signals from the X-ray detector 204 in order to execute rotational radiography and generate X-ray projection data. Although FIG. 7 does not show processing circuitry to perform the steps of method 100, the reconstruction of a CT image to suppress artifacts arising from outside objects according to the methods described herein can be performed using similar processing circuitry (e.g., a CPU) to what is described with reference to FIG. 6.

While certain implementations have been described, these implementations have been presented by way of example only, and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure. The accompanying claims and their equivalents are intended to cover.

The invention claimed is:

1. A computed tomography (CT) imaging apparatus to reduce artifacts in reconstructed CT images, the apparatus comprising:
  processing circuitry configured to
    obtain projection data representing an intensity of radiation detected at a plurality of detector elements, the radiation having been transmitted through a space including a first object, which is at least partially within a field of view (FOV) of a reconstructed image,
    generate an image representing an attenuation of the radiation within the FOV,
    determine difference data including a difference between a forward projection of the image and the projection data, and iteratively reconstruct the image by updating the image to minimize a cost function of the image, the cost function including a de-emphasis operator operating on the difference data, wherein the de-emphasis operator decreases a contribution of the difference data arising from attenuation outside the FOV relative a contribution of the difference data arising from attenuation within the FOV.

2. The apparatus according to claim 1, wherein the processing circuitry is further configured to iteratively reconstruct the image, wherein the difference data has one or more indicia of an artifact arising from the attenuation outside the FOV, and the de-emphasis operator shifts a minimum of the cost function towards the image for which the one or more indicia are minimized.

3. The apparatus according to claim 2, wherein the one or more indicia represent a degree of sharp features in a spatial distribution of the difference data.

4. The apparatus according to claim 1, wherein the processing circuitry is further configured to iteratively reconstruct the image by the de-emphasis operator performing edge-enhancement of the difference data, high-pass filtering the difference data, and/or a first-order derivative of the difference data.

5. The apparatus according to claim 1, wherein the processing circuitry is further configured to iteratively reconstruct the image by the de-emphasis operator operating on the difference data to decrease a low-frequency component of the difference data.

6. The apparatus according to claim 1, wherein the processing circuitry is further configured to iteratively reconstruct the image, wherein the cost function includes a sum of a data fidelity term and a second term including a power of a p-norm of the de-emphasis operator operating on the difference data.

7. The apparatus according to claim 2, wherein the processing circuitry is further configured to iteratively reconstruct the image by the de-emphasis operator evaluating the difference data to emphasize components of the difference data corresponding to sinusoids of a sinogram having amplitudes less than a predefined amplitude.

8. The apparatus according to claim 2, wherein the processing circuitry is further configured to iteratively reconstruct the image by evaluating the difference data to emphasize linear components of the difference data in a sinogram corresponding to lines less than a predefined slope.

9. The apparatus according to claim 2, wherein the one or more indicia of the artifact correspond to an artifact caused by the one or more second objects having a high-attenuation density and a sharp edge.

10. A computed tomography (CT) scanner, comprising:
an X-ray source fixed to an end of a C-arm and configured to emit X-rays in a cone beam;
an X-ray detector fixed to another end of the C-arm, the X-ray detector being configured diametrically opposed to the X-ray source to detect, using a plurality of detector elements, the X-rays emitted in the cone beam, and generating projection data representing an intensity of the X-rays detected at the plurality of detector elements;
an opening provided between the X-ray source and the X-ray detector to accommodate a first object, which is at least partially within a field of view (FOV) of a reconstructed image to be reconstructed from the projection data; and processing circuitry configured to
generate an image representing an attenuation of the radiation within the FOV,
determine difference data including a difference between a forward projection of the image and the projection data, and
iteratively reconstruct the image by updating the image to minimize a cost function of the image, the cost function including a de-emphasis operator operating on the difference data, wherein
the de-emphasis operator decreases a contribution of the difference data arising from attenuation outside the FOV relative a contribution of the difference data arising from attenuation within the FOV.

11. A method, comprising:
obtaining projection data representing an intensity of radiation detected at a plurality of detector elements, the radiation having been transmitted through a space including a first object, which is at least partially within a field of view (FOV) of a reconstructed image;
generating an image representing an attenuation of the radiation within the FOV,
determining difference data including a difference between a forward projection of the image and the projection data; and
iteratively reconstructing the image by updating the image to minimize a cost function of the image, the cost function including a de-emphasis operator operating on the difference data, wherein
the de-emphasis operator decreases a contribution of the difference data arising from attenuation outside the FOV relative a contribution of the difference data arising from attenuation within the FOV.

12. The method according to claim 11, wherein the iteratively reconstructing the image includes that the difference data has one or more indicia of an artifact arising from the attenuation outside the FOV, and the de-emphasis operator shifts a minimum of the cost function towards the image for which the one or more indicia are minimized.

13. The method according to claim 12, wherein the one or more indicia include sharp edges and/or high-spatial-frequency components in the difference data.

14. The method according to claim 11, wherein the iteratively reconstructing the image includes that the de-emphasis performs edge-enhancement of the difference data, high-pass filtering the difference data, and/or a first-order derivative of the difference data.

15. The method according to claim 11, wherein the iteratively reconstructing the image includes that the de-emphasis operator operates on the difference data to decrease a low-frequency component of the difference data.

16. The method according to claim 11, wherein the iteratively reconstructing the image includes that the cost function comprises a sum of a data fidelity term and a second term including a power of a p-norm of the de-emphasis operator operating on the difference data.

17. The method according to claim 12, wherein the iteratively reconstructing the image includes that the de-emphasis operator operates on the difference data to emphasize components of the difference data corresponding to sinusoids of a sinogram having amplitudes less than a predefined amplitude.

18. The method according to claim 12, wherein the iteratively reconstructing the image includes that the de-emphasis operator operates on the difference data to emphasize linear components of the difference data in a sinogram corresponding to lines less than a predefined slope.

19. The method according to claim 12, wherein the one or more indicia include an artifact caused by the one or more second objects having a high-attenuation density and a sharp edge.

20. A non-transitory computer-readable medium storing executable instructions, wherein the instructions, when executed by processing circuitry, cause the processing circuitry to perform the method according to claim 11.

* * * * *

UNITED STATES PATENT AND TRADEMARK OFFICE
CERTIFICATE OF CORRECTION

Page 1 of 1

PATENT NO. : 10,789,738 B2
APPLICATION NO. : 16/179751
DATED : September 29, 2020
INVENTOR(S) : Xiaochuan Pan et al.

It is certified that error appears in the above-identified patent and that said Letters Patent is hereby corrected as shown below:

In the Specification

In Column 1, after Line 15, insert:
-- STATEMENT REGARDING FEDERALLY SPONSORED RESEARCH OR DEVELOPMENT
This invention was made with government support under grant numbers CA158446, CA182264, and EB018102 awarded by the National Institutes of Health. The government has certain rights in the invention. --

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*